United States Patent
Le Besque et al.

(10) Patent No.: US 10,981,269 B2
(45) Date of Patent: Apr. 20, 2021

(54) ANCILLARY HANDLE AND SURGICAL INSTRUMENTATION SET COMPRISING SUCH AN ANCILLARY HANDLE

(71) Applicant: NOVASTEP, St Gregoire (FR)

(72) Inventors: Rémi Le Besque, Bruz (FR); Loïc Girod, Goven (FR); Wilfried Dulin, Crevin (FR)

(73) Assignee: NOVASTEP, St. Gregoire (FR)

( * ) Notice: Subject to any disclaimer, the term of this patent is extended or adjusted under 35 U.S.C. 154(b) by 0 days.

(21) Appl. No.: 15/574,139

(22) PCT Filed: Jul. 11, 2016

(86) PCT No.: PCT/FR2016/051780
§ 371 (c)(1),
(2) Date: Nov. 14, 2017

(87) PCT Pub. No.: WO2017/009570
PCT Pub. Date: Jan. 19, 2017

(65) Prior Publication Data
US 2018/0125469 A1 May 10, 2018

(30) Foreign Application Priority Data

Jul. 16, 2015 (FR) ..................................... 15/56720

(51) Int. Cl.
*B25G 3/02* (2006.01)
*A61B 17/00* (2006.01)
(Continued)

(52) U.S. Cl.
CPC ............ *B25G 3/02* (2013.01); *A61B 17/8875* (2013.01); *B25G 3/18* (2013.01); *A61B 17/00* (2013.01);
(Continued)

(58) Field of Classification Search
CPC ..... B25F 1/00; B25F 1/02; B25F 1/04; B25G 3/02; B25G 3/12; B25G 3/24; B25G 3/26; B25G 3/18; B25G 3/20; B25G 3/28
(Continued)

(56) References Cited

U.S. PATENT DOCUMENTS 3,869,741 A * 3/1975 Logan ....................... B25F 1/00
7/158
4,924,733 A * 5/1990 McKenzie .............. B25B 15/02
81/177.4
(Continued)

FOREIGN PATENT DOCUMENTS

DE 10 2004 012417 A1 4/2005

OTHER PUBLICATIONS

Oct. 31, 2016 International Search Report issued in International Patent Application No. PCT/FR2016/051780.

*Primary Examiner* — Emily M Morgan
(74) *Attorney, Agent, or Firm* — Oliff PLC

(57) ABSTRACT

A ancillary handle includes: a gripping part of the ancillary handle, a receiving part having an elongate seat for the shank, and a locking device for locking the shank and fixing the surgical instrument to the ancillary handle. A locking part engages in a groove on the outer surface of the shank. The locking part translates between: iii) a locking configuration, in which the locking part engages in the groove and blocks the surgical instrument, and iv) an unlocking configuration, in which the locking part frees the shank. The locking device includes an actuation part for moving the locking part between the locking and unlocking configurations.

14 Claims, 3 Drawing Sheets

(51) Int. Cl.
  *A61B 17/88* (2006.01)
  *B25G 3/18* (2006.01)
  *B25G 3/12* (2006.01)
  *B25G 3/26* (2006.01)

(52) U.S. Cl.
  CPC .............. *A61B 2017/00464* (2013.01); *A61B 2017/00477* (2013.01); *B25G 3/12* (2013.01); *B25G 3/26* (2013.01)

(58) Field of Classification Search
  USPC ................................ 600/197, 213, 226, 234
  See application file for complete search history.

(56) References Cited

U.S. PATENT DOCUMENTS

| | | | | |
|---|---|---|---|---|
| 5,470,180 A * | 11/1995 | Jore | ................... | B23B 31/1071 279/14 |
| 5,954,463 A * | 9/1999 | Jore | ................... | B23B 31/1071 408/239 R |
| 6,254,305 B1 * | 7/2001 | Taylor | ..................... | B25G 1/04 15/144.4 |
| 6,327,942 B1 * | 12/2001 | Mariol | ................... | B25G 1/085 81/177.4 |
| 6,461,074 B2 * | 10/2002 | Taylor | ..................... | B25G 1/04 15/144.4 |
| 6,702,530 B2 * | 3/2004 | Bennage | ............... | B23B 45/006 408/241 R |
| 6,715,211 B1 * | 4/2004 | Chi | ........................ | B23D 51/10 30/329 |
| 2001/0024594 A1 * | 9/2001 | Taylor | ..................... | B25G 1/04 403/109.7 |
| 2002/0035901 A1 * | 3/2002 | Anderson | ............... | B25B 23/12 81/439 |
| 2003/0001387 A1 * | 1/2003 | Tawara | ................... | A47L 9/242 285/328 |
| 2011/0041346 A1 * | 2/2011 | Chen | ....................... | B25D 3/00 30/167 |
| 2012/0130388 A1 * | 5/2012 | Plotkin | .............. | A61B 17/8875 606/104 |
| 2013/0096568 A1 * | 4/2013 | Justis | ................ | A61B 17/8875 606/104 |
| 2013/0276240 A1 * | 10/2013 | Gresham | ................ | B25F 1/006 7/138 |
| 2015/0158154 A1 * | 6/2015 | Chen | ....................... | B25B 13/56 206/377 |

* cited by examiner

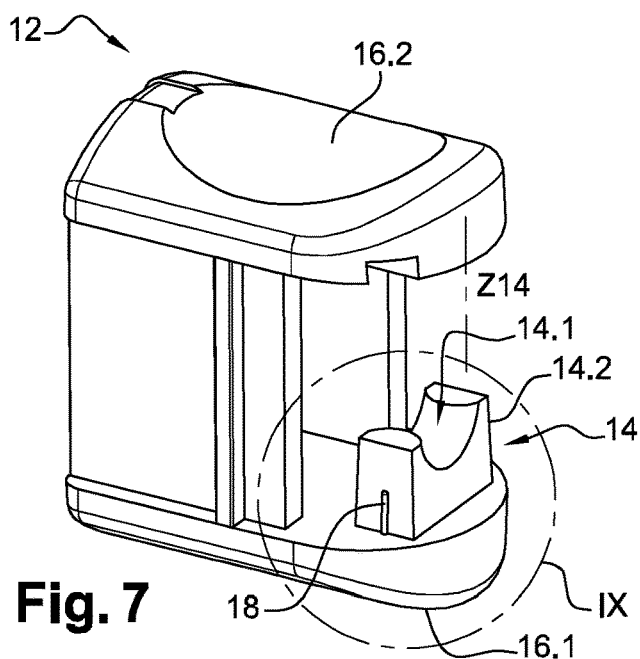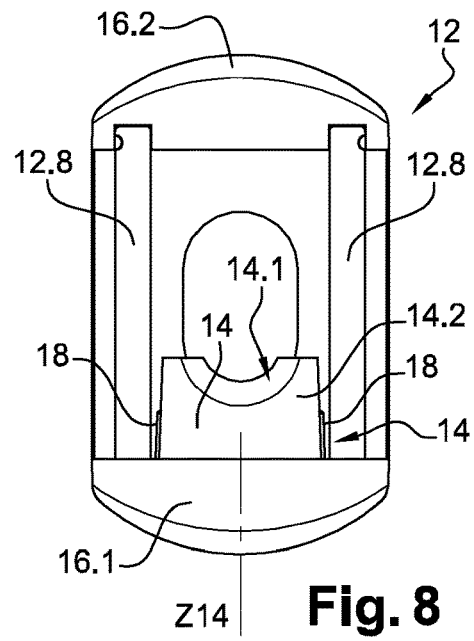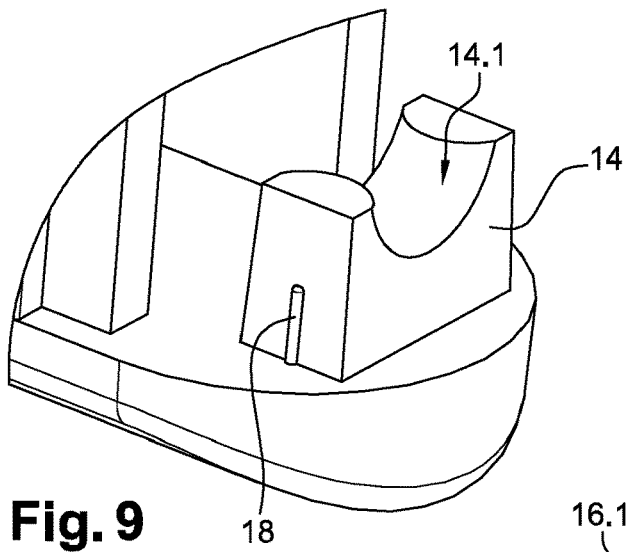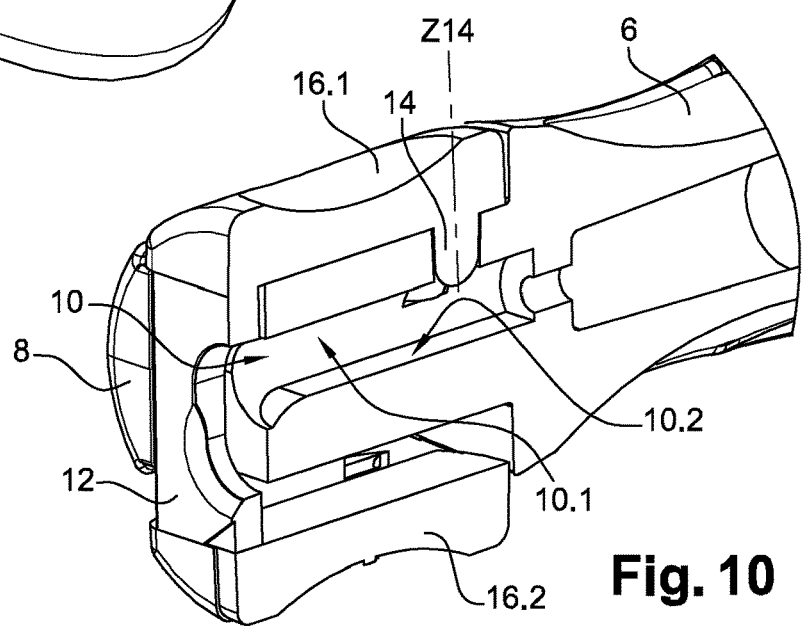

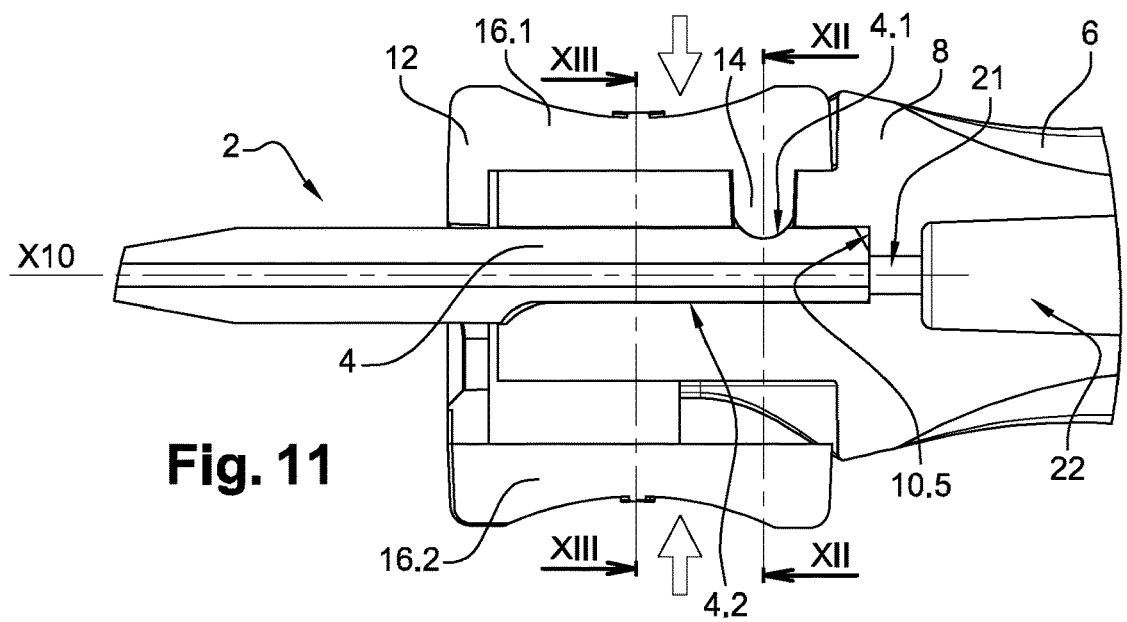
Fig. 11
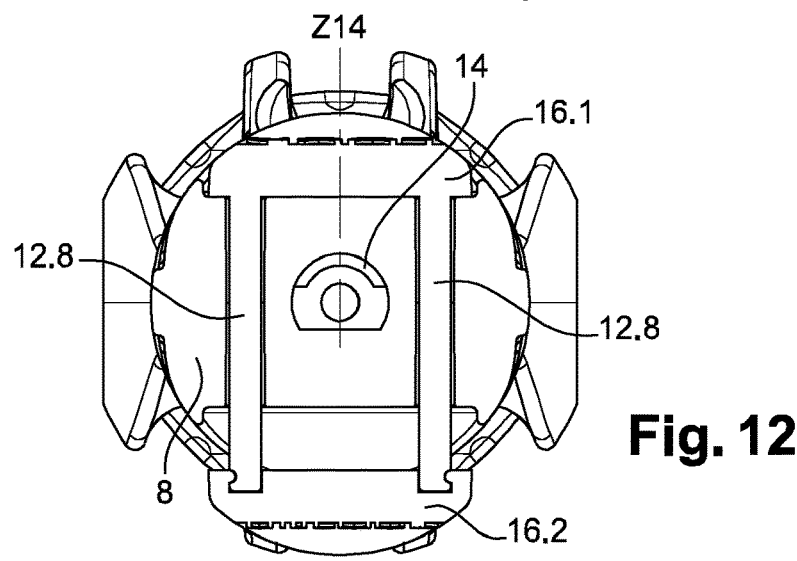
Fig. 12
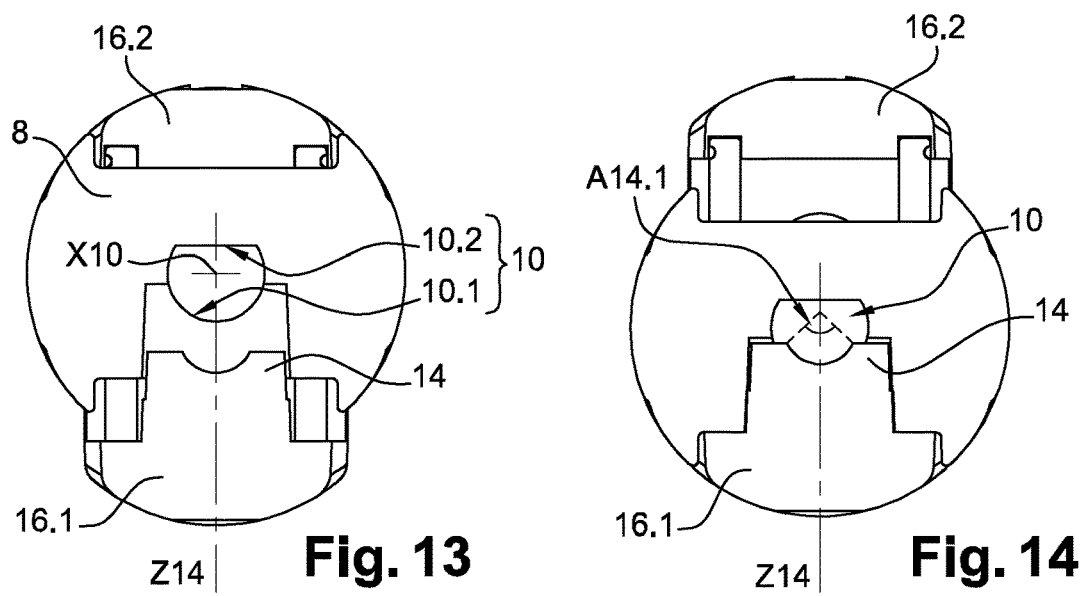
Fig. 13
Fig. 14

ANCILLARY HANDLE AND SURGICAL INSTRUMENTATION SET COMPRISING SUCH AN ANCILLARY HANDLE

The present invention concerns an ancillary handle for manipulating a surgical instrument. In addition, the present invention concerns a surgical instrumentation set comprising such an ancillary handle.

It is known from the state of the art an ancillary composed of an ancillary handle and of a surgical instrument attached to the ancillary handle. The ancillary handle comprises a gripping part and a receiving part having an elongate housing configured to house the rod of the surgical instrument. The ancillary handle further comprises a locking device configured to rapidly lock the rod in the elongate housing so as to attach the surgical instrument to the ancillary handle. The locking device comprises:

balls penetrating into the groove,
springs for urging the balls toward the groove,
an annular ring for guiding the balls, and
an actuating member for displacing the annular ring.

However, such a locking device requires numerous and small parts, which makes the ancillary handle expensive, complex and fragile.

The aim of the present invention is in particular to solve, in whole or in part, the problems mentioned above.

For this purpose, the object of the present invention is an ancillary handle, for manipulating a surgical instrument including a rod, the ancillary handle comprising:

a gripping part configured to allow an operator to manipulate the ancillary handle,
a receiving part having an elongate housing configured to house at least partially the rod, and
a locking device configured to rapidly lock the rod in the elongate housing so as to attach the surgical instrument to the ancillary handle;
the ancillary handle being characterized in that the locking device comprises a locking part configured to penetrate into a groove situated on the outer surface of the rod, the locking part is displaceable in a direction of translation with respect to the receiving part and between:

i) a locking configuration, wherein the locking part can penetrate into the groove, so that the locking device can block the surgical instrument in the elongate housing, and
ii) an unlocking configuration, wherein the locking part can leave the groove, so that the locking part can release the rod,
and in that the locking device further comprises an actuating part arranged to displace the locking part between the locking configuration and the unlocking configuration, the actuating part is secured to the locking part.

Thus, such an ancillary handle is inexpensive to manufacture and reliable, because it does not have balls or other movable parts for locking the surgical instrument. Such an ancillary handle makes it possible to form an ancillary after having rapidly attached the surgical instrument to the ancillary handle. The ancillary handle allows a surgeon to manipulate the surgical instrument.

When the locking part has penetrated into the groove of the rod, the ancillary handle retains the surgical instrument. In particular, the ancillary handle allows attaching standard surgical instruments having a conventional "AO" type connection. The conventional "AO" type connection is sometimes referred to as "AO quick coupling", of the name of the AO Foundation (in German: "Arbeitsgemeinschaft für Osteosynthesefragen").

According to one variant, the direction of translation is rectilinear.

According to one variant, the locking device is connected to the receiving part. The connection between the locking device and the receiving part is selected so as to allow a translation of the locking part. For example, the connection between the locking device and the receiving part may be a slide connection.

The locking device may block the surgical instrument in the elongate housing so as to prevent a translation of the surgical instrument in a direction of elongation of the elongate housing.

According to one embodiment, the elongate housing has a shape comprising an angular cylinder portion and a flat section, the flat section being adapted to cooperate with a complementary flat section situated on the outer surface of the rod, so as to prevent a rotation of the rod in the elongate housing.

Thus, such an elongate housing makes it possible to house and retain part of the rod while preventing the rotation of the rod.

According to one embodiment, the direction of translation extends in a plane perpendicular to the direction of elongation of the elongate housing.

Thus, such a direction of translation makes it possible to form a space-saving locking device in the direction of elongation of the elongate housing.

According to one embodiment, the locking part has an amplitude of displacement comprised between 2 mm and 8 mm.

Thus, such an amplitude of displacement is minimized, thereby allowing a quick locking and unlocking by the surgeon.

According to one embodiment, the locking part has a partially toroidal surface so as to penetrate into the groove of a partially toroidal complementary shape.

Thus, such a partially toroidal surface makes it possible to maximize the contact interface between the locking part and the groove. Therefore, the ancillary handle is adapted to retain standard surgical instruments with a conventional "AO" type connection, with a toroidal or partially toroidal groove.

According to one embodiment, the partially toroidal surface extends over an angular sector comprised between 40 degrees and 180 degrees, the apex of the angular sector belonging to the axis of revolution of the partially toroidal surface.

Thus, the partially toroidal surface on such an angular sector makes it possible to firmly retain the rod in the housing, and therefore to effectively lock the surgical instrument in the ancillary rod. Indeed, such an angular sector provides the partially toroidal surface with a contact interface extended with the groove of the rod.

According to one variant, the partially toroidal surface is formed by an inner torus portion. According to one variant, the partially toroidal surface has a circular arc-like base.

According to one embodiment, the actuating part and the receiving part are situated at one end of the gripping part.

In other words, the actuating part is situated near the receiving part. Thus, the ancillary handle is ergonomic, as the surgeon can easily manipulate the actuating part, unlike an actuating part of the state of the art situated opposite the receiving part, therefore opposite the rod, with respect to the gripping part.

In addition, the ancillary handle offers a highly safe manipulation because the surgeon is not likely to unlock the surgical instrument unexpectedly by exerting a pressure on the gripping part; while the state of the art has sometimes an actuating part situated on a portion of the receiving part on which the surgeon often exerts a pressure, which may unexpectedly unlock the surgical instrument.

According to one embodiment, the actuating part comprises a lock button and an unlock button, the lock button being arranged to displace the locking part toward the locking configuration, the unlock button being arranged to displace the locking part toward the unlocking configuration.

Thus, such locking and unlock buttons facilitate the manipulation of the ancillary handle by a surgeon, for example between the thumb and the forefinger.

According to one embodiment, the lock button and the unlock button are secured to each other and situated on two opposite sides of the elongate housing.

In other words, the lock button and the unlock button are displaced symmetrically and somehow operate in phase opposition. Thus, the surgeon can easily manipulate the actuating part because the locking and unlocking gestures are symmetrical.

According to one embodiment, the locking device includes at least one immobilization part, the immobilization part being secured in translation with the locking part, so that the immobilization part is movable between:

i) an immobilization state, wherein the immobilization part allows an immobilization of the locking device with respect to the receiving part when the locking part is in the locking configuration, and ii) a release state, wherein the immobilization part releases the locking device from the receiving part when the locking part is in the unlocking configuration, the immobilization part being configured to authorize a maximum number of immobilizations, so that the immobilization part no longer allows immobilization when the maximum number is reached.

Thus, such an immobilization part authorizes only one use of ancillary handle in a limited number, therefore limited in time, for example limited to a surgical operation, which guarantees the safety of the patient, because there is no risk of unexpected re-use of the ancillary handle which would be no more sterile.

According to one embodiment, the maximum number is comprised between 5 and 50, for example between 5 and 20.

Thus, the ancillary handle is practically for single use.

According to one embodiment, the immobilization part is configured to undergo a plastic deformation, for example by caulking, during each immobilization, so that the immobilization part is worn when the maximum number is reached.

Thus, such a plastically deformable immobilization part makes it possible to limit immobilizations to the maximum number.

According to one embodiment, the locking part has a base, the immobilization part comprising at least an over-thickness of material which extends on a respective side of the base.

Thus, such an over-thickness of material makes it possible to limit the number of immobilization, because the over-thickness of material is caulked, and therefore partially flattened, at each immobilization. The dimensions of the over-thickness of material can be selected according to the mechanical properties of the material (coefficient of friction, hardness) and to the required locking sensation.

and the receiving part are composed of a material selected from the group consisting of polyarylamides (PAA, for example IXEF®) and polyphenylsulfones (PPSA, for example RADEL®).

According to one variant, the immobilization part comprises two over-thicknesses of material which extend respectively over two opposite sides of the base. For example, the over-thicknesses of material can be formed by gadroons. Each over-thickness of material may have a rectilinear shape extending substantially parallel to the direction of translation.

Alternatively, the immobilization part comprises a tapered surface and the receiving part has a complementary tapered housing, the tapered surface and the tapered housing being configured to carry out a Morse taper type-fitting.

According to one embodiment, the receiving part has a primary passage and the gripping part has a secondary passage, the primary passage and the secondary passage match so as to make a guide pin pass through the primary and secondary passages.

Thus, a surgeon can temporarily implant guide pins, and then thread a cannulated surgical instrument and the ancillary handle on the guide pin, in order to guide his gesture in an accurate manner.

Furthermore, the object of the present invention is a surgical instrumentation set comprising:

an ancillary handle according to the invention, and several surgical instruments each including a rod, the outer surface of each rod having a groove adapted to receive the locking part, so that the surgical instruments are interchangeable.

Thus, such a surgical instrumentation set allows an easy manipulation by the surgeon and the ancillary handle is cost-effective and safe.

According to one embodiment, the outer surface of the gripping part has longitudinal slots, each longitudinal slot being adapted to house the rod of a respective surgical instrument so as to attach said surgical instrument by elastic snap-fit.

Thus, the surgical instrumentation set is compact, which facilitates its transport and storage.

The embodiments and variants mentioned above can be taken separately or according to any technically possible combination.

The present invention will be well understood and its advantages will also appear in view of the following description, given only by way of non-limiting example and made with reference to the appended schematic figures, wherein identical reference signs correspond to structurally and/or functionally identical or similar elements. In the appended schematic figures:

FIG. 7 is a perspective view of a locking device belonging to the ancillary handle of FIG. 1;

FIG. 8 is a front view of the locking device of FIG. 7;

FIG. 9 is a view on a larger scale of the detail IX in FIG. 8;

FIG. 10 is a truncated perspective view of a part of the locking device of FIG. 1 in a locking configuration;

FIG. 11 is a section of the part illustrated in FIG. 10;

FIG. 12 is a section along the line XII in FIG. 11, in a locking configuration;

FIG. 13 is a section along the line XIII in FIG. 11, in an unlocking configuration; and FIG. 14 is a section similar to FIG. 13, in a locking configuration.

Figure 1:
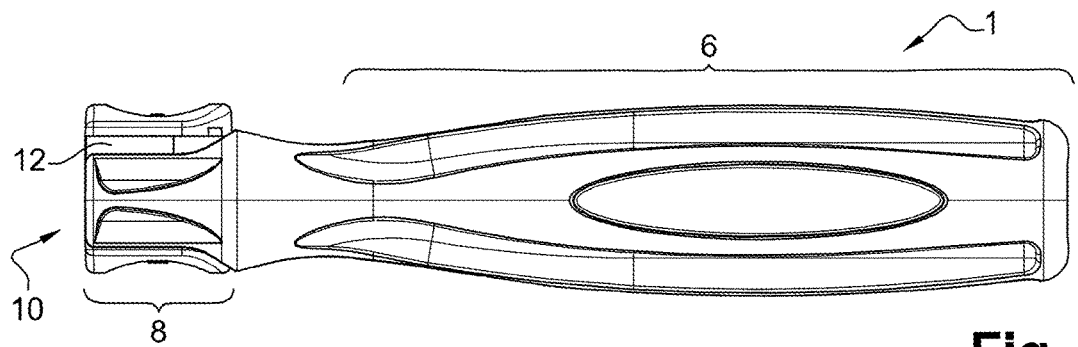
FIG. 1 is a side view of an ancillary handle in accordance with the invention.

FIGS. 1 to 14 illustrate an ancillary handle 1 for manipulating a surgical instrument 2 including a rod 4. The ancillary handle 1 equipped with a surgical instrument 2 forms a surgical instrumentation set 100.

The ancillary handle 1 comprises a gripping part 6, a receiving part 8 and a locking device 12. The gripping part 6 is configured to allow an operator to manipulate the ancillary handle 1. The receiving part 8 has an elongate housing 10 which is configured to house at least partially the rod 4. The locking device 12 is configured to rapidly lock the rod 4 in the elongate housing 10 so as to attach the surgical instrument 2 to the ancillary handle 1.

The locking device 12 comprises a locking part 14 which is configured to penetrate into a groove 4.1 situated on the outer surface of the rod 4. The locking part 14 is displaceable in a direction of translation Z14 with respect to the receiving part 8. The locking part 14 is movable between:

iii) a locking configuration (FIGS. 2, 6, 10, 11 and 14), wherein the locking part 14 can penetrate into the groove 4.1, so that the locking device 12 can block the surgical instrument 2 in the elongate housing 10, and iv) an unlocking configuration (FIGS. 3, 12 and 13), wherein the locking part 14 can leave the groove 4.1, so that the locking part 14 can release the rod 4.

The direction of translation Z14 is rectilinear and extends in a plane P14 perpendicular to the direction of elongation X10 of the elongate housing 10. The locking part 14 has an amplitude of displacement approximately equal to 5 mm parallel to the direction of translation Z14.

Figures 2, 3:
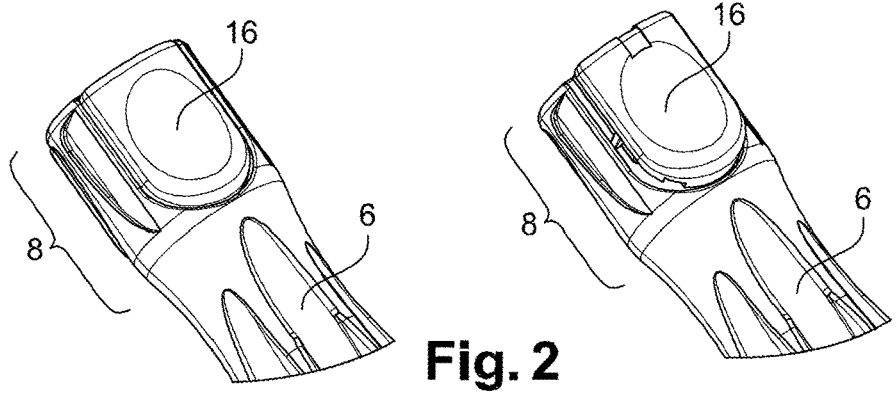
FIGS. 2 and 3 are perspective views from two opposite angles, of a part of the ancillary handle of FIG. 1.
Figure 4:
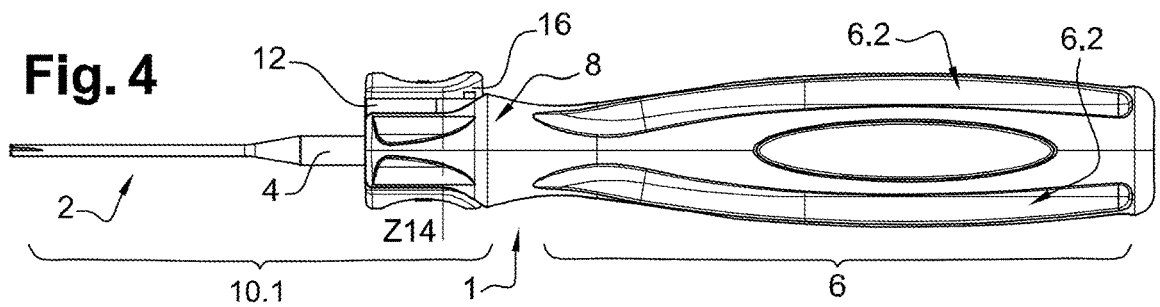
FIG. 4 is a side view of a surgical instrumentation set in accordance with the invention, in a service configuration and comprising the ancillary handle of FIG. 1.

The locking device 12 further comprises an actuating part 16. The actuating part 16 is arranged to displace the locking part 14, in the direction of translation Z14, between the locking configuration (FIGS. 2, 6, 10, 11 and 14) and the unlocking configuration (FIGS. 3, 12 and 13).

The locking device 12 is connected to the receiving part 8. The connection between the locking device 12 and the receiving part 8 is selected so as to allow a translation of the locking part 14. In the example of the figures, the connection between the locking device 12 and the receiving part 8 is a slide or sliding connection 12.8.

The actuating part 16 is secured to the locking part 14. The actuating part 16 and the receiving part 8 are here situated at the same end of the gripping part 6, which makes the ancillary handle 1 ergonomic.

The receiving part 8 has a primary passage 21 and the gripping part 6 has a secondary passage 22. The primary passage 21 and the secondary passage 22 match so as to allow the passage of a same guide pin through the primary passage 21 and the secondary passage 22.

The actuating part 16 comprises a lock button 16.1 and an unlock button 16.2. The lock button 16.1 and the unlock button 16.2 are here secured to each other and situated on two opposite sides of the elongate housing 10.

The lock button 16.1 is arranged to displace the locking part 14 toward the locking configuration (FIGS. 2, 6, 10, 11 and 14). The unlock button 16.2 is arranged to displace the locking part 14 toward the unlocking configuration (FIGS. 3, 12 and 13).

The lock button 16.1 and the unlock button 16.2 are displaced symmetrically and operate in phase opposition.

Thus, such locking 16.1 and unlocking 16.2 buttons facilitate the manipulation of the ancillary handle 1 by a surgeon, between the thumb and the forefinger.

Figure 5:
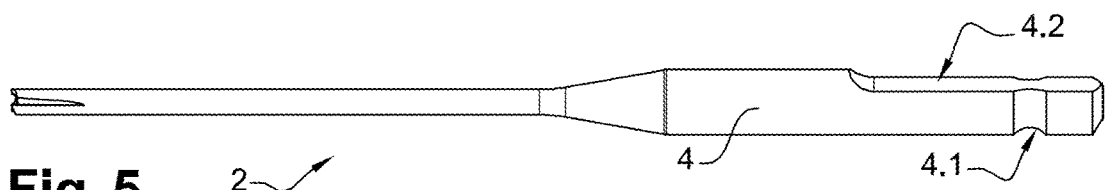
FIG. 5 is a side view of a surgical instrument belonging to the surgical instrumentation set of FIG. 4.
Figure 6:
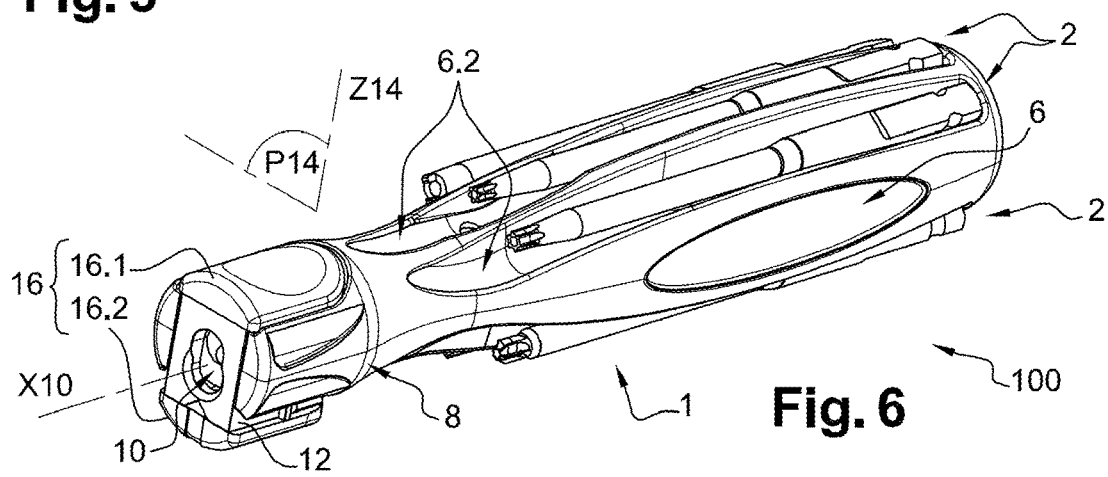
FIG. 6 is a perspective view of the surgical instrumentation set of FIG. 4, in a storage configuration.

As illustrated in FIGS. 5 and 10, the elongate housing 10 has a shape comprising an angular cylinder portion 10.1 and a flat section 10.2. The flat section 10.2 is adapted to cooperate with a complementary flat section 4.2 situated on the outer surface of the rod 4, so as to prevent rotation of the rod 4 in the elongate housing 10.

In addition, the elongate housing 10 has a mechanical stop 10.5 which has the function of positioning the surgical instrument 2 in the ancillary handle 1 according to the longitudinal direction of elongation X10.

Thus, thanks to the cooperation of the flat sections 4.2 and 10.2, the elongate housing 10 makes it possible to house and retain part of the rod 4 while preventing the rotation of the rod 4.

As illustrated in FIGS. 7, 8 and 9, the locking part 14 has a partially toroidal surface 14.1 which is configured to penetrate into the groove 4.1, which groove has a partially toroidal complementary shape. In the example of the figures, the partially toroidal surface 14.1 is formed by an inner torus portion, with a circular arc-like base.

As shown in FIG. 1, the partially toroidal surface 14.1 extends over an angular sector A14.1 approximately equal to 120 degrees. The apex of the angular sector A14.1 belonging to the axis of revolution of the partially toroidal surface 14.1. The partially toroidal surface 14.1 is referred to as partially toroidal due to its extension over an angular sector which is less than 360 degrees.

Thus, the partially toroidal surface 14.1 makes it possible to maximize the contact interface between the locking part 14 and the groove 4.1. Therefore, the ancillary handle 1 is adapted to retain standard surgical instruments 2 with a conventional "AO" type connection.

When the locking part 14 has penetrated into the groove 4.1 of the rod 4, the ancillary handle 1 retains the surgical instrument 2, and therefore immobilizes the surgical instrument 2 in translation in the direction of elongation X10.

Furthermore, the locking device 12 includes an immobilization part 18 which is secured in translation to the locking part 14, so that the immobilization part 18 is displaceable between:

iii) an immobilization state, wherein the immobilization part 18 allows an immobilization of the locking device 12 with respect to the receiving part 8 when the locking part 14 is in the locking configuration (FIGS. 2, 6, 10, 11 and 14), and iv) a release state, wherein the immobilization part 18 releases the locking device 12 from the receiving part 8 when the locking part 14 is in the unlocking configuration (FIGS. 3, 12 and 13).

The immobilization part 18 is configured to authorize a maximum number of immobilizations, so that the immobilization part 18 no longer allows immobilization when the maximum number is reached. The maximum number is here approximately equal to 20.

Thus, the immobilization part 18 authorizes only one use of the ancillary handle 1 which is limited in time, for example limited to a surgical operation.

The immobilization part 18 is here configured to undergo a plastic deformation by caulking during each immobilization of a surgical instrument 2, so that the immobilization part 18 is worn when the maximum number (here 20) is reached.

The locking part 14 has a base 14.2. The immobilization part 18 comprises two over-thicknesses of material which extend respectively on both sides of the base 14.2. The over-thicknesses of material are here formed by gadroons each having a rectilinear shape extending substantially parallel to the direction of translation Z14.

These over-thicknesses of material make it possible to limit the number of immobilization. Indeed, each over-thickness of material is caulked, therefore partially flattened, at each immobilization.

Furthermore, the object of the present invention is a surgical instrumentation set 100 comprising the ancillary handle 1 and several surgical instruments 2. Each of the surgical instruments 2 includes a rod 4, whose outer surface has a groove 4.1. As specified above, the groove 4.1 is adapted to receive the locking part 14, so that the surgical instruments 2 are interchangeable.

The outer surface of the gripping part 6 has longitudinal slots 6.2. Each longitudinal slot 6.2 is adapted to house the rod 4 of a respective surgical instrument 2, so as to attach this surgical instrument 2 by elastic snap-fit.

Of course, the present invention is not limited to the particular embodiments described in the present patent application, nor to embodiments within the reach of those skilled in the art. Other embodiments can be considered without departing from the scope of the invention, from any element equivalent to an element indicated in the present patent application.

The invention claimed is:

1. An ancillary handle, for manipulating a surgical instrument including a rod, the ancillary handle comprising:
    a gripping part configured to allow an operator to manipulate the ancillary handle,
    a receiving part having an elongate housing configured to at least partially house the rod, and
    a locking device configured to rapidly lock the rod in the elongate housing so as to attach the surgical instrument to the ancillary handle;
    the locking device comprising
        a locking part configured to penetrate into a groove situated on the outer surface of the rod, the locking part being displaceable in a direction of translation with respect to the receiving part and between:
            i) a locking configuration, wherein the locking part can penetrate into the groove, so that the locking device can block the surgical instrument in the elongate housing, and
            ii) an unlocking configuration, wherein the locking part can leave the groove, so that the locking part can release the rod, and
        an actuating part configured to displace the locking part between the locking configuration and the unlocking configuration, the actuating part being firmly fixed to the locking part,
    wherein the locking device further includes an immobilization part secured to a base of the locking part so that the immobilization part is displaceable between:
        i) an immobilization state, wherein the immobilization part cooperates with the receiving part and immobilizes the locking device with respect to the receiving part, the immobilization part being in the immobilization state when the locking part is in the locking configuration, and
        ii) a release state, wherein the immobilization part releases the locking device from the receiving part, the immobilization part being in the release state when the locking part is in the unlocking configuration,
    the immobilization part comprising two protrusions extending respectively on both sides of the base of the locking part, the protrusions being configured to undergo a plastic deformation each time the immobilization part is displaced in the immobilization state and cooperates with the receiving part, the plastic deformation configured to allow a maximum number of times in the immobilization state, so that the locking device cannot cooperate with the receiving part when the maximum number is reached,
    wherein the locking part has a base, the immobilization part comprising two protrusions extending respectively on both sides of the base, the protrusions being configured to undergo a plastic deformation each time the immobilization part is displaced in the immobilization state and cooperates with the receiving part.

2. The ancillary handle according to claim 1, wherein each protrusion has a rectilinear shape extending parallel to the direction of translation of the locking part.

3. The ancillary handle according to claim 1, wherein the maximum number is from 5 to 50.

4. The ancillary handle according to claim 1, wherein the actuating part is movable in translation along a displacement direction which extends in a plane perpendicular to a direction of elongation of the elongate housing.

5. The ancillary handle according to claim 1, wherein the actuating part is integral with the locking part.

6. The ancillary handle according to claim 1, wherein the elongate housing has a shape comprising an angular cylinder portion and a flat section, the flat section being adapted to cooperate with a complementary flat section situated on the outer surface of the rod, so as to prevent a rotation of the rod in the elongate housing.

7. The ancillary handle according to claim 1, wherein the direction of translation of the locking part extends in a plane perpendicular to a direction of elongation of the elongate housing.

8. The ancillary handle according to claim 1, wherein the locking part is configured to have an amplitude of displacement comprised between 2 mm and 8 mm.

9. The ancillary handle according to claim 1, wherein the locking part has a partially toroidal surface so as to penetrate into the groove of a partially toroidal complementary shape.

10. The ancillary handle according to claim 9, wherein the partially toroidal surface extends over an angular sector comprised between 40 degrees and 180 degrees, the apex of the angular sector belonging to the axis of revolution of the partially toroidal surface.

11. The ancillary handle according to claim 1, wherein the actuating part and the receiving part are situated at the same end of the gripping part.

12. The ancillary handle according to claim 1, wherein the actuating part comprises a lock button and an unlock button, the lock button being configured to displace the locking part toward the locking configuration, the unlock button being configured to displace the locking part toward the unlocking configuration.

13. The ancillary handle according to claim 12, wherein the lock button and the unlock button are secured to each other and situated on two opposite sides of the elongate housing.

14. The ancillary handle according to claim 1, wherein the receiving part has a primary passage and the gripping part has a secondary passage that matches with the primary passage.

* * * * *